US011484279B2

(12) United States Patent
Vija et al.

(10) Patent No.: US 11,484,279 B2
(45) Date of Patent: Nov. 1, 2022

(54) SYSTEMS TO ASSESS PROJECTION DATA INCONSISTENCY

(71) Applicant: Siemens Medical Solutions USA, Inc., Malvern, PA (US)

(72) Inventors: Alexander Hans Vija, Evanston, IL (US); Xinhong Ding, Buffalo Grove, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 776 days.

(21) Appl. No.: 16/409,967

(22) Filed: May 13, 2019

(65) Prior Publication Data

US 2020/0093454 A1    Mar. 26, 2020

Related U.S. Application Data

(60) Provisional application No. 62/735,431, filed on Sep. 24, 2018.

(51) Int. Cl.
*A61B 6/00* (2006.01)
*G06N 3/08* (2006.01)
*G06T 7/238* (2017.01)
*A61B 6/03* (2006.01)

(52) U.S. Cl.
CPC ............. *A61B 6/5205* (2013.01); *G06N 3/08* (2013.01); *G06T 7/238* (2017.01); *A61B 6/037* (2013.01); *A61B 6/5264* (2013.01); *G06T 2207/10108* (2013.01); *G06T 2207/20081* (2013.01)

(58) Field of Classification Search
CPC ..... A61B 6/5205; A61B 6/037; A61B 6/5264; G06T 7/2308; G06T 2207/10108; G06T 2207/20081; G06N 3/08
See application file for complete search history.

(56) References Cited

U.S. PATENT DOCUMENTS

| | | | |
|---|---|---|---|
| 2003/0128801 A1* | 7/2003 | Eisenberg | A61B 6/466 378/19 |
| 2007/0048326 A1 | 3/2007 | Cairns et al. | |
| 2007/0237290 A1* | 10/2007 | Mostafavi | A61B 6/025 378/21 |
| 2010/0232645 A1 | 9/2010 | Blaffert et al. | |
| 2010/0289813 A1 | 11/2010 | Nobe et al. | |
| 2011/0142314 A1 | 6/2011 | Hsieh et al. | |
| 2011/0228897 A1 | 9/2011 | Kobayashi | |
| 2012/0169333 A1 | 7/2012 | Katscher et al. | |
| 2013/0034286 A1 | 2/2013 | Vija et al. | |

(Continued)

FOREIGN PATENT DOCUMENTS

| | | |
|---|---|---|
| CN | 1408102 A | 4/2003 |
| CN | 101167662 A | 4/2008 |

(Continued)

*Primary Examiner* — Khai M Nguyen

(57) ABSTRACT

A system and method include acquisition of a plurality of projection images of a subject, each of the projection images associated with a respective projection angle, determination, for each of the projection images, of a center-of-light location in a first image region, determination of a local fluctuation measure based on the determined center-of-light locations, and determination of a quality measure associated with the plurality of projection images based on the local fluctuation measure.

20 Claims, 8 Drawing Sheets

(56) References Cited

U.S. PATENT DOCUMENTS

| | | |
|---|---|---|
| 2013/0315459 A1 | 11/2013 | Wollenweber et al. |
| 2014/0072194 A1 | 3/2014 | Hansis et al. |
| 2014/0355855 A1 | 12/2014 | Miao et al. |
| 2015/0302616 A1 | 10/2015 | Hu et al. |
| 2016/0095565 A1 | 4/2016 | Fenchel |
| 2016/0125605 A1 | 5/2016 | Lee et al. |
| 2016/0203609 A1 | 7/2016 | Wang |
| 2016/0220311 A1 | 8/2016 | Mansi et al. |
| 2017/0193159 A1 | 7/2017 | Cachovan et al. |
| 2017/0209112 A1 | 7/2017 | Yi et al. |
| 2017/0219674 A1 | 8/2017 | Van Der Kouwe et al. |
| 2017/0278280 A1 | 9/2017 | Ben-Haim |
| 2017/0360325 A1 | 12/2017 | Hebert |
| 2018/0025512 A1 | 1/2018 | Zhu et al. |
| 2018/0033166 A1 | 2/2018 | Cachovan et al. |
| 2018/0056091 A1 | 3/2018 | Jordan et al. |
| 2018/0336677 A1 | 11/2018 | Sloan et al. |

FOREIGN PATENT DOCUMENTS

| | | |
|---|---|---|
| CN | 101408976 A | 4/2009 |
| CN | 102846326 A | 1/2013 |
| CN | 102982510 A | 3/2013 |
| CN | 103136734 A | 6/2013 |
| CN | 103417234 A | 12/2013 |
| CN | 104169969 A | 11/2014 |

\* cited by examiner $$\delta_k = \frac{|ax_k + by_k + c|}{\sqrt{a^2 + b^2}}$$

$$a = \frac{y_{k+1} - y_{k-1}}{x_{k+1} - x_{k-1}}, \quad b = -1, \quad c = \frac{x_{k+1}y_{k-1} - x_{k-1}y_{k+1}}{x_{k+1} - x_{k-1}}$$

SYSTEMS TO ASSESS PROJECTION DATA INCONSISTENCY

CROSS-REFERENCE TO RELATED APPLICATIONS

The present application is related to and claims priority to U.S. Provisional Patent Application No. 62/735,431, filed Sep. 24, 2018, the contents of which are incorporated by reference in their entirety, for all purposes.

BACKGROUND

In emission imaging such as single-photon-emission-computer-tomography (SPECT), detectors rotate around a patient to acquire a set of projection images based on radiation emitted from the patient. Three-dimensional images are reconstructed from the set of projection images using known techniques. The three-dimensional images may be used for diagnosis and/or treatment planning.

Acquisition of the projection images may be performed over a timespan of a few minutes to several hours, during which the patient is likely to move. Patient motion during projection image acquisition may result in data inconsistency between the projection images. A three-dimensional image reconstructed from these projection images may exhibit poor quality and thereby hinder accurate diagnosis and treatment. If this three-dimensional image is reconstructed after the patient has been released from the scanning theater, the patient may have to return for another scan at a later time.

Conventionally, a technician may visually assess data inconsistency among projection images prior to releasing the patient. This approach is subjective and technician-dependent, and does not provide consistent or reliably repeatable results. Systems are desired to efficiently quantify data inconsistency among a set of projection images, preferably prior to image reconstruction.

DETAILED DESCRIPTION

Figure 1:
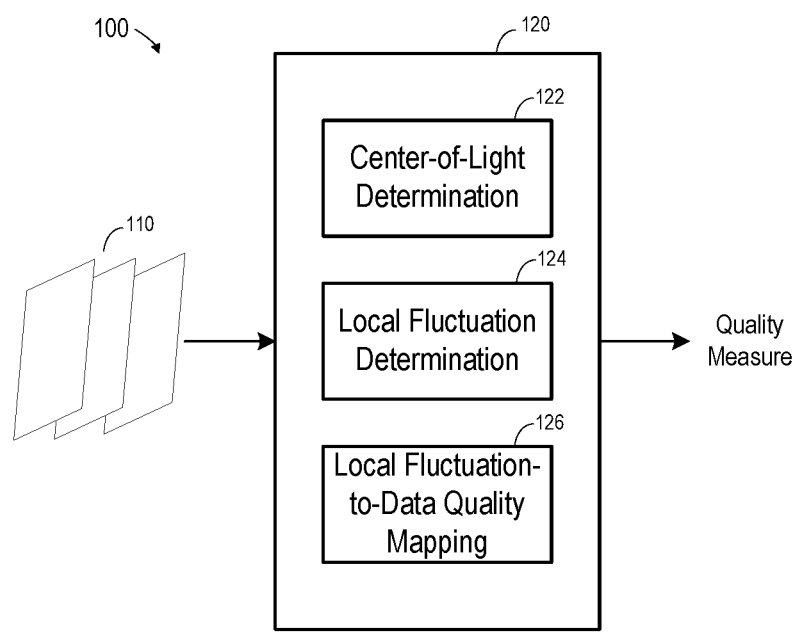
FIG. 1 is a block diagram of a system to generate a quality measure based on projection images according to some embodiments.

The following description is provided to enable any person in the art to make and use the described embodiments and sets forth the best mode contemplated for carrying out the described embodiments. Various modifications, however, will remain apparent to those in the art.

Embodiments may provide technical improvements over existing systems by efficiently evaluating data inconsistency between projection images. Consequently, implementations may avoid reconstruction of images based on inconsistent data and/or signal the desirability of re-scanning a patient prior to releasing the patient from the scanning theater.

Some embodiments provide a system to assess the data consistency of projection images, for example those acquired for purposes of reconstructing a three-dimensional image therefrom. Generally, the coordinates of one or more center-of-light (CL) locations are determined for each projection image. Fluctuations of the coordinates between successive images are determined and a measure of data inconsistency (e.g., represented by a measure of data quality) is determined based on the determined fluctuations.

Intuitively, if the set of projection images is acquired with proper count density and with no patient motion, the coordinates of the CL locations should not change drastically among adjacent projection images. Conversely, any patient motion or other device abnormality may cause a non-negligible change in CL location coordinates among some adjacent projection images. Data quality of a dense and complex set of data (i.e., a set of projection images) may therefore be determined based on a much smaller set of data (i.e., coordinates of the one or more CL locations).

According to some embodiments, a mapping is used to determine a measure of data quality based on the determined fluctuations. The mapping may be generated based on determinations of local fluctuations within historical sets of projection images depicting many different types of motion, and in human-generated characterizations of the quality of images reconstructed from each of the historical sets of projection images. Some embodiments may alternatively use the determined local fluctuations of the historical sets of projection images and corresponding human-generated characterizations to train an artificial neural network to generate a quality measure based on one or more input fluctuation measures. Generally, the mapping maps a first small set of data (i.e., fluctuation measures) representing a dense and complex set of data (i.e., a set of projection images) to another small set of data (i.e., the human-generated characterizations) representing the dense and complex set of data.

Embodiments may be used to analyze sets of projection images of any suitable type and acquired by any suitable means. A set of projection images according to some embodiments represents n-dimensional space using k (n−1)-dimensional images, where k is the number of different projection angles from which each (n−1)-dimensional image is acquired.

FIG. 1 is a block diagram of system 100 according to some embodiments. System 100 receives a set of projection images 110, each of which depicts a subject from a respective projection angle. Projection images 110 may include any number of projection images. Although embodiments are described herein with respect to projection images generated based on radioactive emissions, embodiments may be implemented in conjunction with transmission images (e.g., computed tomography, X-ray) and any other type of images including pixels associated with brightness values, regardless of imaging modality.

Quality determination unit 120 receives projection images 110 of a patient, for example. Quality determination unit 120 includes center-of-light determination component 122, local fluctuation determination component 124 and local fluctuation-to-data quality mapping component 126. Briefly, center-of-light determination component 122 determines the coordinates of one or more CL locations for each of projection images 110. Local fluctuation determination component 124 determines one or more measures of local fluctuation coordinates between successive ones of projection images 110 based on their respective CL location coordinates. Next, local fluctuation-to-data quality mapping component 126 maps the one or more measures of local fluctuation coordinates to a data quality measure. The data quality measure may be used to determine whether to re-scan the patient or to proceed with image reconstruction based on projection images 110. Each of the foregoing processes will be described in detail below.

Each unit, component or other functional system described herein may be implemented by one or more computing devices (e.g., computer servers), storage devices (e.g., hard or solid-state disk drives), and other hardware as is known in the art. These components may be located remote from one another and may be elements of one or more cloud computing platforms, including but not limited to a Software-as-a-Service, a Platform-as-a-Service, and an Infrastructure-as-a-Service platform.

Figure 2:
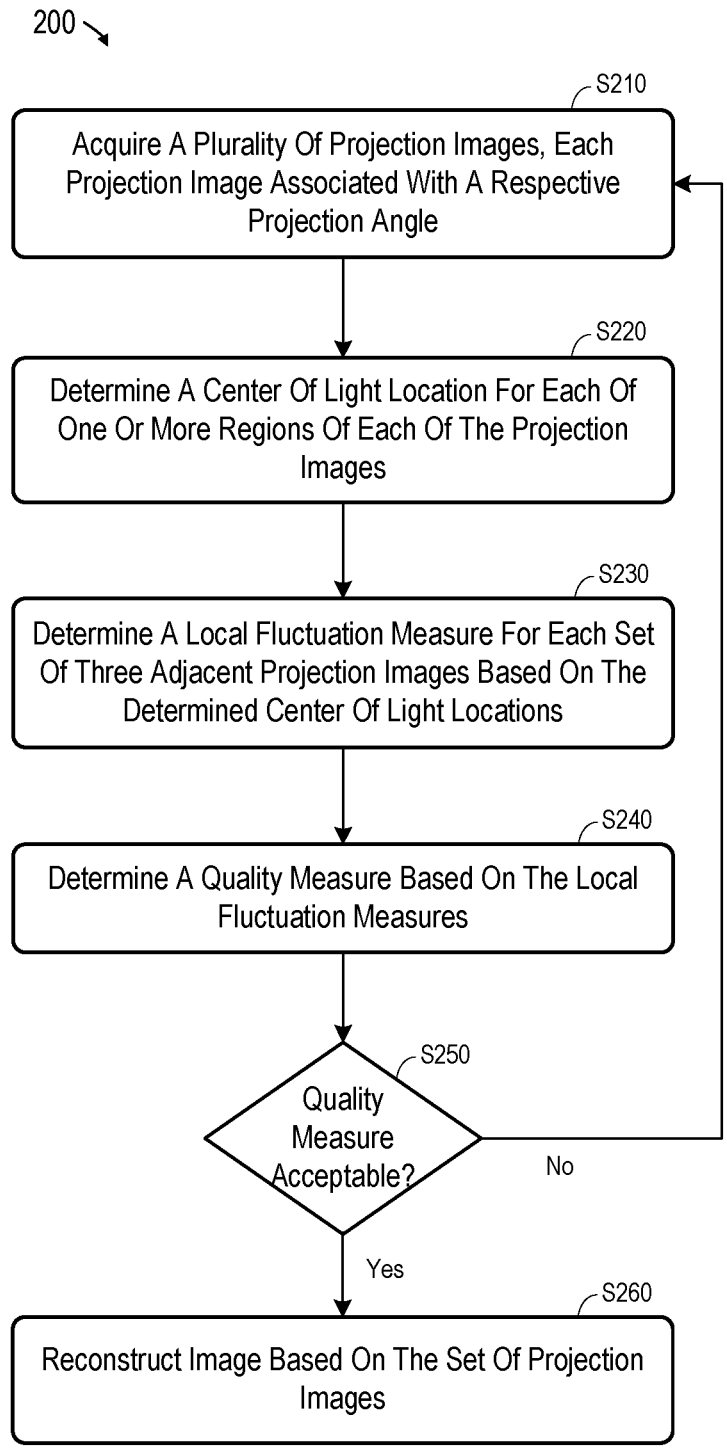
FIG. 2 is a flow diagram of a process to evaluate the quality of projection images prior to image reconstruction according to some embodiments.

FIG. 2 is a flow diagram of a process according to some embodiments. Process 200 and the other processes described herein may be performed using any suitable combination of hardware and software. Software program code embodying these processes may be stored by any non-transitory tangible medium, including a fixed disk, a volatile or non-volatile random access memory, a CD, a DVD, a Flash drive, or a magnetic tape. Embodiments are not limited to the examples described below.

Initially, a plurality of projection images are acquired at S210. Each projection image is associated with a respective projection angle. For example, a SPECT detector may rotate around a patient and receive gamma ray emissions therefrom at each of a plurality of projection angles. The emissions received at a projection angle are used to generate an image associated with the projection angle. In other embodiments, an X-ray source transmits X-rays through the patient toward a detector at each projection angle.

The projection images may be acquired at S210 by an imaging system which also performs the remaining steps of process 200. In some embodiments, the projection images were acquired by an imaging system in the past and are acquired at S210 (e.g., via a Flash drive or network connection) by a computing system which performs the remaining steps of process 200. Prior to performing the remaining steps, the projection images may be subjected to preprocessing such as image denoising. Image denoising may be particularly desirable if the count densities of the images are low.

For each projection image, a CL location is determined at S220 for each of one or more image regions. Generally, the CL location of an image region is determined based on weighted values of each image pixel in the region, wherein the weight of an image pixel is based on its associated brightness (or other visual characteristic) value. The weighted distribution of image pixels in the region should be roughly similar in all directions around the CL location in some embodiments. The CL location may be therefore be considered roughly analogous to the center of mass of a physical object.

Figure 3A:
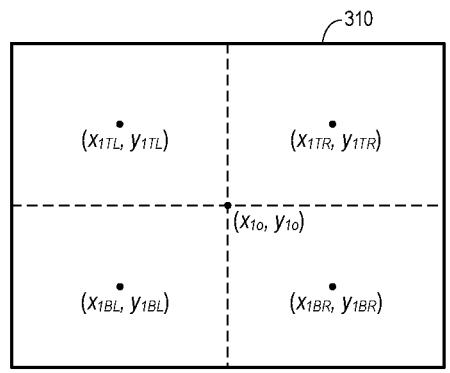
FIG. 3a is a representation of a center-of-light locations within regions of a projection image according to some embodiments.
Figure 3B:
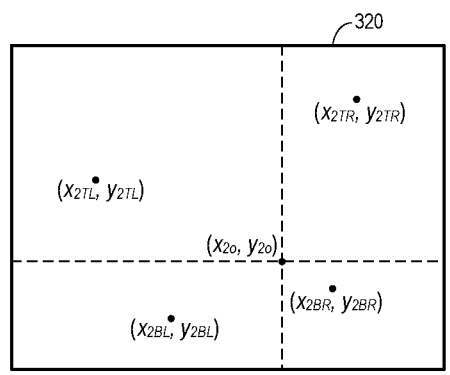
FIG. 3b is a representation of a center-of-light locations within regions of a projection image according to some embodiments.

According to some embodiments, a first "global" CL location is determined for an entire projection image, four image regions are determined based on the global CL location, and a local CL location is determined for each of the four image regions. FIGS. 3a and 3b illustrate the determination of CL locations for projection image 310 and projection image 320 according to some embodiments. Referring to FIG. 3a, the global CL location is defined by coordinate $(x_{1o}, y_{1o})$. As shown, image 310 is logically divided into four image regions (i.e., Top Right, Top Left, Bottom Right and Bottom Left) based on the x- and y-coordinates of the global CL location. A local CL location is determined within each region based on the pixel values of the region. As shown, the coordinates of the local CL locations of each of the image regions are $(x_{1TL}, y_{1TL})$, $(x_{1TR}, y_{1TR})$, $(x_{1BL}, y_{1BL})$, and $(x_{1BR}, y_{1BR})$.

The global CL location of projection image 320 of FIG. 3 is defined by coordinate $(x_{2o}, y_{2o})$. Image 320 is also logically divided into four image regions (i.e., Top Right, Top Left, Bottom Right and Bottom Left) based on the x- and y-coordinates of the global CL location. However, unlike projection image 310, the sizes of the regions differ because the coordinate $(x_{2o}, y_{2o})$ of the global CL location is not the physical center of image 320. The coordinates of the local CL locations determined for each of the image regions are $(x_{2TL}, y_{2TL})$, $(x_{2TR}, y_{2TR})$, $(x_{2BL}, y_{2BL})$, and $(x_{2BR}, y_{2BR})$.

The following is an explanation of the determination of the coordinates of the five CL locations of projection images 310 and 320 according to some embodiments. It is assumed that the two-dimensional image array A is expressed as a function on some closed discrete subset in the X-Y plane:

$$\mathbb{V} = [x_{min}, x_{max}] \times [y_{min}, y_{max}], \text{ where}$$

$$A = \{I(x, y) : x, y \text{ are positive integers with } (x, y) \in \mathbb{V}\}$$

The center of light of A may be defined in some embodiments as:

$$x_{CL}(\mathbb{V}) = \frac{1}{N} \sum_{(x,y) \in V} x I(x, y)$$

$$y_{CL}(\mathbb{V}) = \frac{1}{N} \sum_{(x,y) \in V} y I(x, y)$$

where $$N = \sum_{(x,y) \in V} I(x, y)$$

Using the above notation, the global CL location is:

$$x_o := x_{CL}(\mathbb{V}), \quad y_o := y_{CL}(\mathbb{V})$$

As illustrated in FIGS. 3a and 3b, the global CL location may be used to determine multiple sub-regions Q of the discrete subset V such as:

$$\mathbb{Q}_{TR} = [x_o, x_{max}] \times [y_{min}, y_o]$$

$$\mathbb{Q}_{TL} = [x_{min}, x_o] \times [y_{min}, y_o]$$

$$\mathbb{Q}_{BL} = [x_{min}, x_o] \times [y_o, y_{min}]$$

$$\mathbb{Q}_{BR} = [x_o, x_{min}] \times [y_o, y_{max}]$$

The CL locations of each of the sub-regions may then be expressed as:

$$(x_1, y_1) := (x_{CL}(Q_{RT}), y_{CL}(Q_{TR}))$$

$$(x_2, y_2) := (x_{CL}(Q_{TL}), y_{CL}(Q_{TL}))$$

$$(x_3, y_3) := (x_{CL}(Q_{BL}), y_{CL}(Q_{BL}))$$

$$(x_4, y_4) := (x_{CL}(Q_{BR}), y_{CL}(Q_{BR}))$$

Embodiments are not limited to four image regions or to image regions defined as described above. For example, a projection image may be divided into regions by two or more angular, curved and/or circular boundaries.

Figure 4:
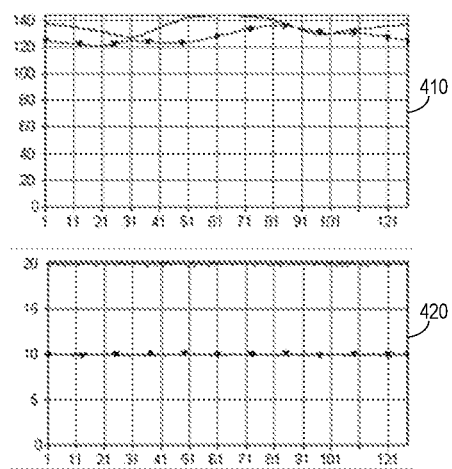
FIG. 4 includes two graphs depicting changes in center-of-light locations for a set of projection images depicting low levels of target motion according to some embodiments.

FIG. 4 shows plot 410 of X and Y coordinates of CL locations over a series of projection images. As expected, the CL locations change due to the changing angular perspectives of the projection images. Plot 420 shows second derivatives of the curves of plot 410. Plot 420 shows that the rate of change of the CL location changes is fairly constant, indicating a lack of substantial subject motion.

Figure 5:
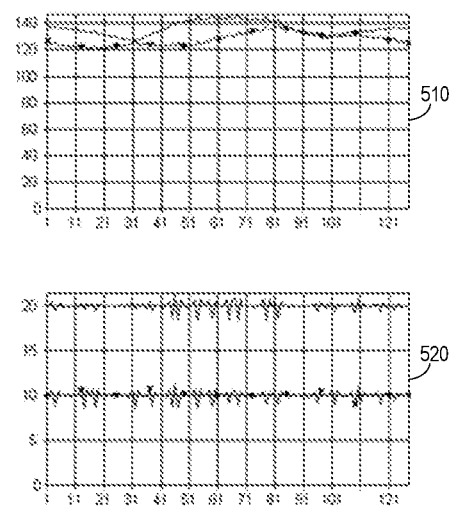
FIG. 5 includes two graphs depicting changes in center-of-light locations for a set of projection images depicting moderate levels of target motion according to some embodiments.

FIG. 5 shows plot 510 of X and Y coordinates of CL locations over a series of projection images, and plot 520 shows second derivatives of the curves of plot 510. Plot 520 shows fluctuations in the second derivative and thereby suggests subject motion during imaging.

Returning to process 200, a local fluctuation measure is determined at S230 for each set of three adjacent projection images based on the determined center of light locations. The determined local fluctuation measure may comprise two or more local fluctuation measures or may be a composite of two or more local fluctuation measures according to some embodiments.

Figure 6:
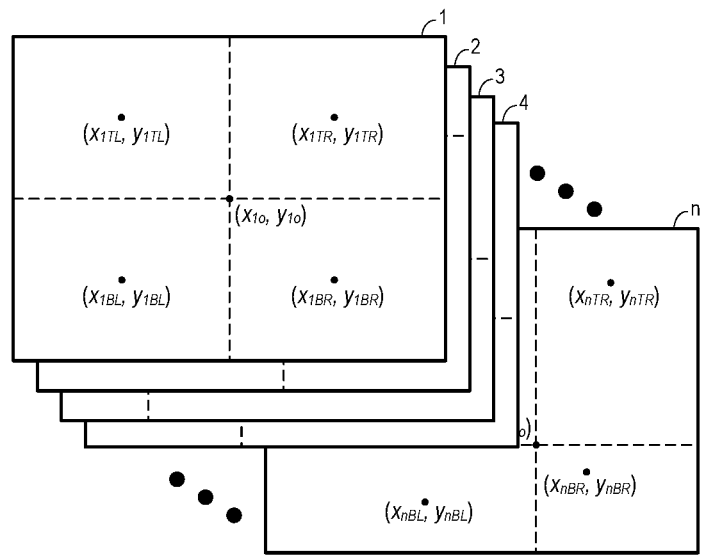
FIG. 6 illustrates a set of projection image images associated with respective center-of-light locations according to some embodiments.

FIG. 6 illustrates projection images 1 through n acquired at S210 according to one example. Each of projection images 1 through n is associated with a different projection angle. It will be assumed that the projection images are numbered in accordance with their order of acquisition. That is, projection image 2 was acquired after projection image 1 and after projection image 3, and is associated with a projection angle between the projection angles associated with projection images 1 and 3.

A global CL location and four local CL locations have been determined for each of projection images 1 through n at S220. As illustrated, the regions of the local CL locations may differ among projection images 1 through n due to difference in the coordinates of their associated global CL locations.

In one example of S230 with respect to projection images 1 through n of FIG. 6, a local fluctuation measure is determined for each region for which CL locations were determined at S220. Specifically, a local fluctuation measure is determined based on coordinates $(x_{1o}, y_{1o})$, $(x_{2o}, y_{2o})$, . . . , $(x_{no}, y_{no})$, a local fluctuation measure is determined based on coordinates $(x_{1TL}, y_{1TL})$, $(x_{2TL}, y_{2TL})$, . . . , $(x_{nTL}, y_{nTL})$, and so on for the coordinates of each CL location determined for regions TR, BL and BR.

Figure 7:
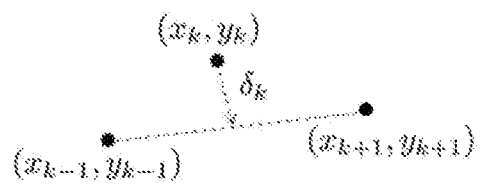
FIG. 7 depicts determination of a local fluctuation measure according to some embodiments.

FIG. 7 illustrates determination of a local fluctuation measure for a single region according to some embodiments. For the $k^{th}$ view in a set of projection images, the local fluctuation measure $\delta_k$ for a region is the distance of the CL location of the $k^{th}$ view to a line connecting the CL locations of the two neighboring views. As shown, the determination of measure $\delta_k$ utilizes three coordinates $(x_{k-1}, y_{k-1})$, $(x_k, y_k)$ and $(x_{k+1}, y_{k+1})$.

With reference to FIG. 6, the three coordinates $(x_{1TL}, y_{1TL})$, $(x_{2TL}, y_{2TL})$ and $(x_{3TL}, y_{3TL})$ may be used to determine $\delta_2$. More specifically, using the illustrated calculations of FIG. 7, measure $\delta_2$ may be calculated for region TL based on the values of $x_{1TL}$, $y_{1TL}$, $x_{2TL}$, $y_{2TL}$, $x_{3TL}$, and $y_{3TL}$. Measure $\delta_k$ may be calculated for each other combination of CL locations of region TL within three successive projection images. Measure $\delta_{k, k=2 \text{ to } n-1}$ may be similarly calculated for each other region, including the global region, of projection images 1 through n.

Therefore, a series of local fluctuation measures may be determined at S230 for each region. According to some embodiments, a single local fluctuation measure is determined for each region by summing the series of measures determined for the region. Any other suitable systems to determine a single local fluctuation measure for each region based on a series thereof may be employed. Moreover, the single local fluctuation measures for each region may be combined (e.g., summed) to determine a single overall local fluctuation measure.

A quality measure is determined based on the local fluctuation measure(s) at S240. The quality measure may be determined based on a mapping between local fluctuation measure(s) and image quality measures.

Figure 8:
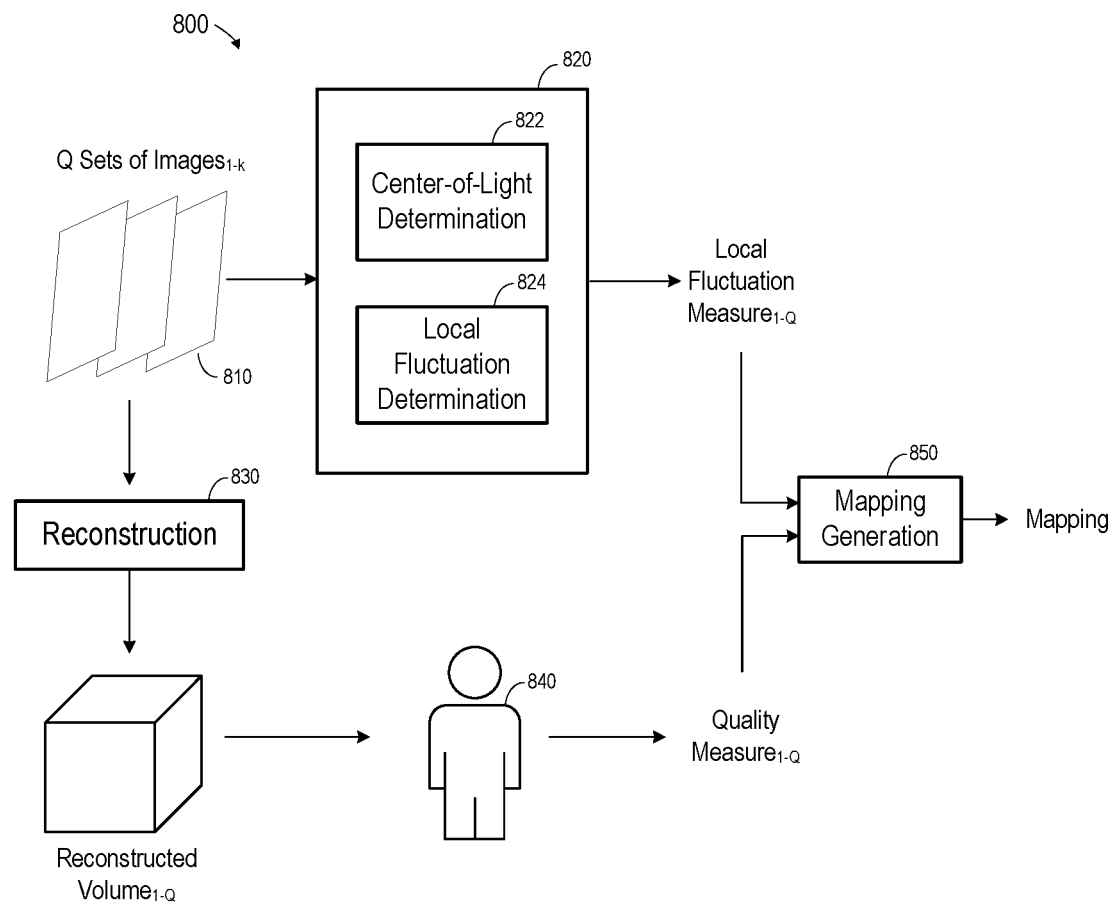
FIG. 8 is a block diagram of a system to generate a fluctuation measure-to-quality measure mapping according to some embodiments.

FIG. 8 illustrates system 800 to generate such a mapping according to some embodiments. Q sets 810 of historical projection images$_{1-k}$ preferably represent different types of motion which may be encountered during subsequent use of the generated mapping as described above. Accordingly, it is desirable that each of Q sets 810 of historical projection images$_{1-k}$ represents some degree of translational or rotational target motion (i.e., from no motion to extreme motion) along any one or more axes.

For each set Q of historical projection images$_{1-k}$, unit 820 determines CL locations (822) and local fluctuation measures (824), resulting in associated local fluctuation measures$_{1-Q}$. Each of local fluctuation measures$_{1-Q}$ may comprise more than one local fluctuation measure (e.g., one fluctuation measure for each projection image region), and is associated with a single set of historical projection images$_{1-k}$.

Each set Q of historical projection images$_{1-k}$ is also subjected to reconstruction (830) to generate an associated one of reconstructed volumes$_{1-Q}$. Human observer 840 inspects each of reconstructed volumes$_{1-Q}$ and determines a quality measure for each reconstructed volume$_{1-Q}$. In some examples, more than one human observer 840 inspects each reconstructed volume and/or each of reconstructed volumes$_{1-Q}$ is inspected by one of any number of human observers 840, each of whom follows a specified protocol for determining a quality measure based on a reconstructed volume.

Accordingly, each set Q of historical projection images$_{1-k}$ is associated with one of local fluctuation measures$_{1-Q}$ and one of quality measures$_{1-Q}$. These associations are used to generate a mapping (850) between the two data types. Accordingly, such a mapping may be used at S240 to determine a quality measure based on a local fluctuation measure.

Figure 9:
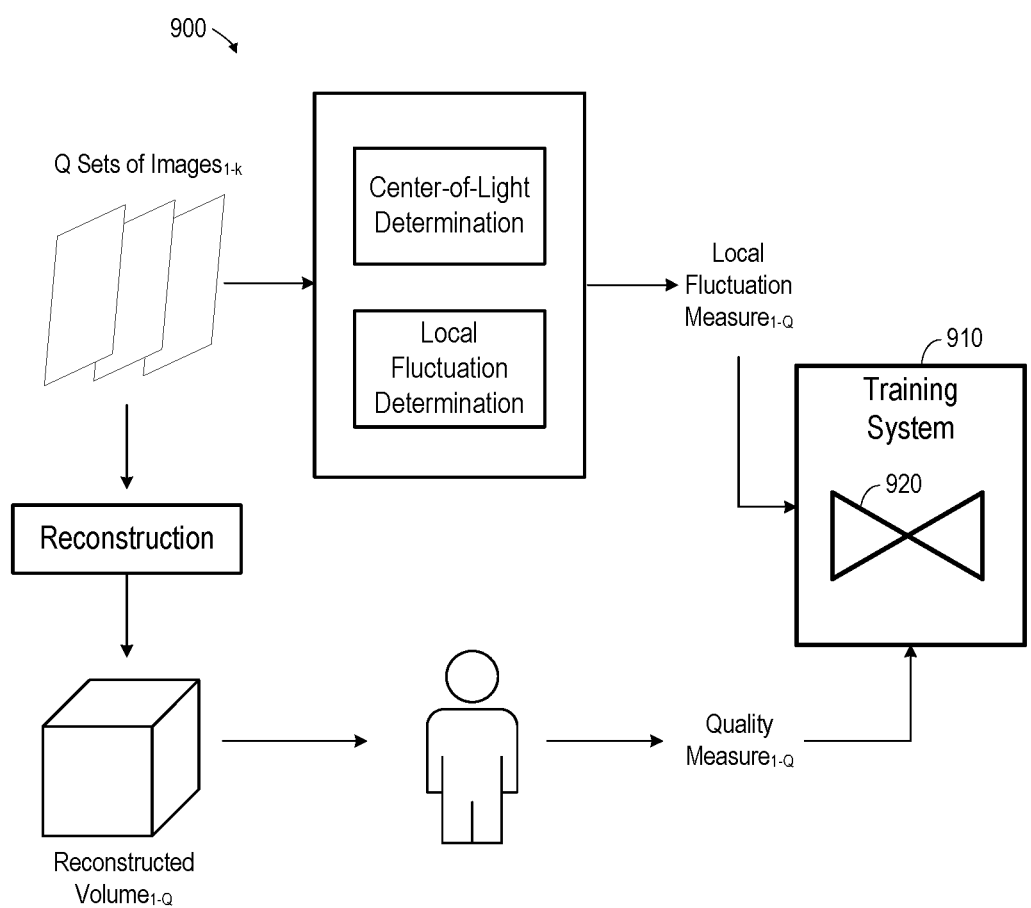
FIG. 9 is a block diagram of a system to train an artificial neural network to generate a quality measure based on an input fluctuation measure according to some embodiments.

FIG. 9 illustrates system 900 according to some embodiments. As illustrated, local fluctuation measures$_{1-Q}$ and associated quality measures$_{1-Q}$ are generated based on Q sets of historical projection images$_{1-n}$ as described above. Local fluctuation measures$_{1-Q}$ and associated quality measures$_{1-Q}$ are input to training system 910 as training data for artificial neural network 920. For example, system 910 may train system 920 such that system 920 substantially outputs one of quality measures$_{1-Q}$ upon receiving its associated local fluctuation measure$_{1-Q}$ as input. According to some embodiments, training system 910 uses CL locations and associated quality measures$_{1-Q}$ as training data, eliminating a need to determine local fluctuations.

Artificial neural network 920 may comprise a network of neurons which receive input, change internal state according to that input, and produce output depending on the input and internal state. The output of certain neurons is connected to the input of other neurons to form a directed and weighted graph. The weights as well as the functions that compute the internal state can be modified by a training process based on ground truth data. Artificial neural network 920 may comprise any one or more types of artificial neural network that are or become known, including but not limited to convolutional neural networks, recurrent neural networks, long short-term memory networks, deep reservoir computing and deep echo state networks, deep belief networks, and deep stacking networks.

In one example, the training of network 920 generates parameter values for kernels of a fully convolutional network. Another fully convolutional network comprising thusly-parameterized kernels may be efficiently incorporated into a system to determine a quality measure at S240 based on a local fluctuation measure.

Returning to process 200, it is determined at S250 if the quality measure is acceptable. For example, the determined quality measure may be compared to a prespecified threshold. The threshold may differ based on the intended usage of the projection images, time constraints, and any other suitable factor. If the quality measure is not acceptable, flow returns to S210 to acquire another set of projection images. As described above, it may be advantageous to determine the unacceptable quality and acquire the other set of images before releasing the patient.

Flow proceeds from S250 to S260 is the quality measure is deemed acceptable. At S260, an image is reconstructed based on the set of projection images. Any suitable reconstructions algorithm may be employed at S260. The reconstructed images may then be used as intended.

Figure 10:
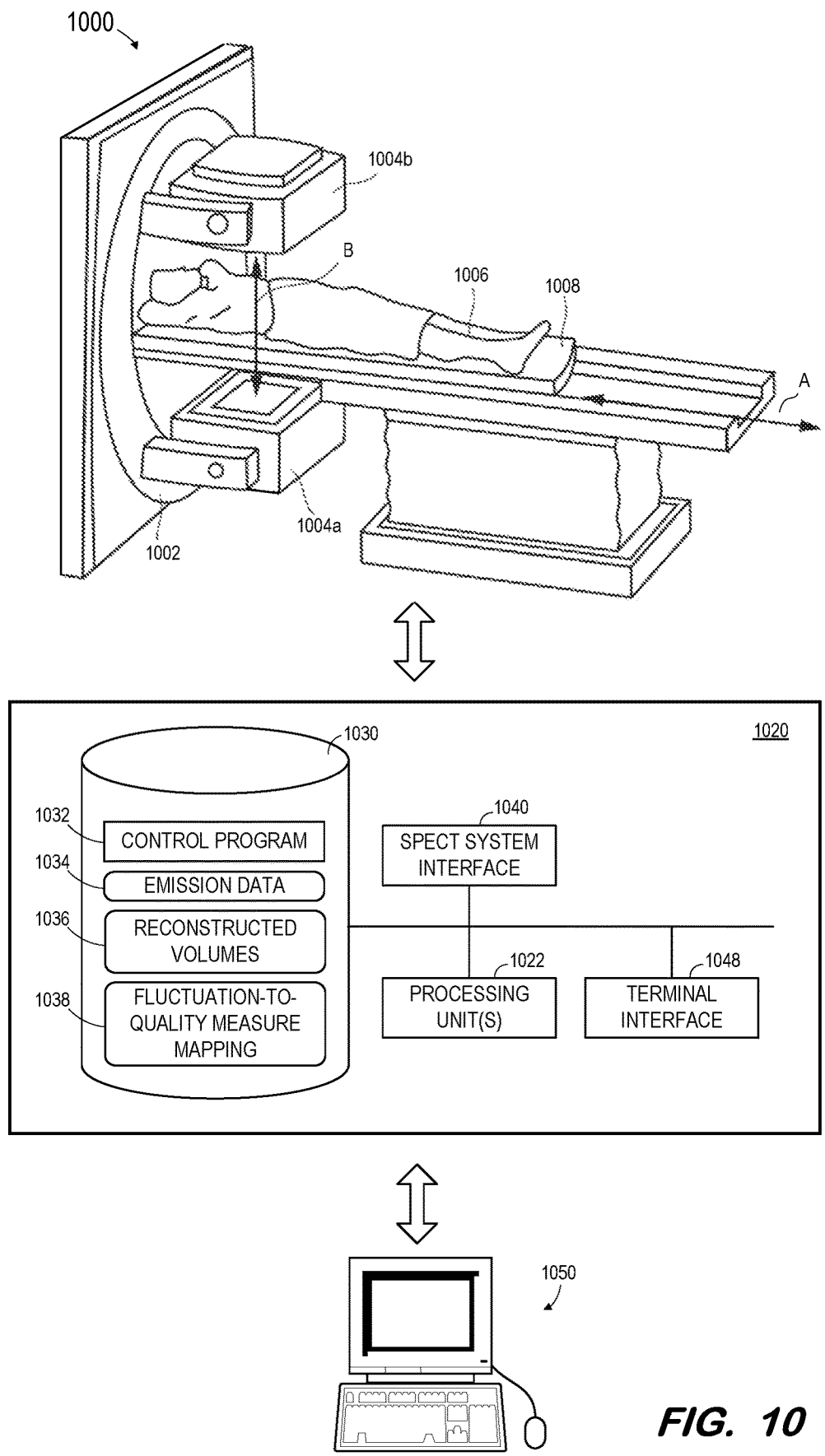
FIG. 10 illustrates a SPECT imaging system according to some embodiments.

FIG. 10 illustrates SPECT system 1000 which may implement process 200 as described above. System 1000 includes gantry 1002 to which two or more gamma cameras 1004a, 1004b are attached, although any number of gamma cameras can be used. A detector within each gamma camera detects gamma photons (i.e., emission data) emitted by a radioisotope within the body of a patient 1006 lying on a bed 1008.

Bed 1008 is capable of moving patient 1006 along axis A and/or axis B. At respective bed positions (i.e., imaging positions), a portion of the body of patient 1006 is positioned between gamma cameras 1004a, 1004b in order to capture emission data from that body portion. Gamma cameras 1004a, 1004b may include multi-focal cone-beam collimators or parallel-hole collimators as is known in the art.

Control system 1020 may comprise any general-purpose or dedicated computing system. Accordingly, control system 1020 includes one or more processing units 1022 configured to execute processor-executable program code to cause system 1020 to operate as described herein, and storage device 1030 for storing the program code. Storage device 1030 may comprise one or more fixed disks, solid-state random access memory, and/or removable media (e.g., a thumb drive) mounted in a corresponding interface (e.g., a USB port).

Storage device 1030 stores program code of system control program 1032. One or more processing units 1022 may execute system control program 1032, in conjunction with SPECT system interface 1040, to control motors, servos, and encoders to cause gamma cameras 1004a, 1004b to rotate along gantry 1002 and to acquire two-dimensional emission data (i.e. projection images) at defined imaging positions during the rotation. The acquired data 1034 may be stored in memory 1030. Control program 1032 may also be executed to reconstruct volumes 1036 from emission data 1034 as is known.

Control program 1032 may also be executed to cause control system 1020 to perform process 200, including determinations of CL locations and of local fluctuation measures. Quality measures may be determined based on fluctuation-to-quality measure mapping 1038, which may comprise convolution kernel parameters of a trained neural network.

Terminal 1050 may comprise a display device and an input device coupled to system 1020. Terminal 1050 may display any of two-dimensional emission data 1034, reconstructed volumes 1036, and local fluctuation measures, and may receive user input for controlling display of the data, operation of imaging system 1000, and/or the processing described herein. In some embodiments, terminal 1050 is a separate computing device such as, but not limited to, a desktop computer, a laptop computer, a tablet computer, and a smartphone.

Each of component of system 1000 may include other elements which are necessary for the operation thereof, as well as additional elements for providing functions other than those described herein.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
   a storage device;
   a processor to execute processor-executable process steps stored on the storage device to cause the system to:
   for each of a plurality of projection images of a subject, each of the projection images associated with a respective projection angle, determine a center-of-light location in a first image region;
   determine a local fluctuation measure based on the determined center-of-light locations; and
   determine a quality measure associated with the plurality of projection images based on the local fluctuation measure.

2. A system according to claim 1,
   wherein determination of the local fluctuation measure is based on differences in the center-of-light locations determined for projection images associated with adjacent projection angles.

3. A system according to claim 1, wherein the processor is to execute processor-executable process steps to cause the system to:
   determine, for each of the projection images, a center-of-light location in a second image region,
   wherein determination of the local fluctuation measure comprises:
   determination of a first local fluctuation measure based on the center-of-light locations determined in the first image region,
   determination of a second local fluctuation measure based on the center-of-light locations determined in the second image region, and
   determination of the local fluctuation measure based on the first local fluctuation measure and the second local fluctuation measure.

4. A system according to claim 3,
wherein determination of the first local fluctuation measure is based on differences in the center-of-light locations determined in the first image region for projection images associated with adjacent projection angles, and
wherein determination of the second local fluctuation measure is based on differences in the center-of-light locations determined in the second image region for projection images associated with adjacent projection angles.

5. A system according to claim 3, wherein the processor is to execute processor-executable process steps to cause the system to:
determine a first center-of-light location for a first one of the projection images;
determine the first region and the second region of the first one of the projection images based on the determined first center-of-light location;
determine a second center-of-light location for a second one of the projection images; and
determine the first region and the second region of the second one of the projection images based on the determined second center-of-light location.

6. A system according to claim 5,
wherein determination of the first local fluctuation measure is based on differences in the center-of-light locations determined in the first image region for projection images associated with adjacent projection angles, and
wherein determination of the second local fluctuation measure is based on differences in the center-of-light locations determined in the second image region for projection images associated with adjacent projection angles.

7. A system according to claim 1, wherein
when it is determined that the quality measure indicates unsuitable quality, the processor executes processor-executable process steps to cause the system to acquire a second plurality of projection images of the subject, and
when it is determined that the quality measure indicates suitable quality, the processor executes processor-executable process steps to cause the system to reconstruct a three-dimensional image based on the plurality of projection images of the subject.

8. A system according to claim 7, wherein determination of the quality measure associated with the plurality of projection images based on the local fluctuation measure comprises inputting the local fluctuation measure to a trained artificial neural network.

9. A method comprising:
for each of a plurality of projection images of a subject, each of the projection images associated with a respective projection angle, determining a center-of-light location in a first image region;
determining a local fluctuation measure based on the determined center-of-light locations; and
determining a quality measure associated with the plurality of projection images based on the local fluctuation measure.

10. A method according to claim 9, wherein determining the local fluctuation measure is based on differences in the center-of-light locations determined for projection images associated with adjacent projection angles.

11. A method according to claim 9, further comprising:
determining, for each of the projection images, a center-of-light location in a second image region,
wherein determining the local fluctuation measure comprises:
determining a first local fluctuation measure based on the center-of-light locations determined in the first image region,
determining a second local fluctuation measure based on the center-of-light locations determined in the second image region, and
determining the local fluctuation measure based on the first local fluctuation measure and the second local fluctuation measure.

12. A method according to claim 11,
wherein determining the first local fluctuation measure is based on differences in the center-of-light locations determined in the first image region for projection images associated with adjacent projection angles, and
wherein determining the second local fluctuation measure is based on differences in the center-of-light locations determined in the second image region for projection images associated with adjacent projection angles.

13. A method according to claim 11, further comprising:
determining a first center-of-light location for a first one of the projection images;
determining the first region and the second region of the first one of the projection images based on the determined first center-of-light location;
determining a second center-of-light location for a second one of the projection images; and
determining the first region and the second region of the second one of the projection images based on the determined second center-of-light location.

14. A method according to claim 13,
wherein determining the first local fluctuation measure is based on differences in the center-of-light locations determined in the first image region for projection images associated with adjacent projection angles, and
wherein determining the second local fluctuation measure is based on differences in the center-of-light locations determined in the second image region for projection images associated with adjacent projection angles.

15. A method according to claim 9, further comprising:
acquiring a second plurality of projection images of the subject when it is determined that the quality measure indicates unsuitable quality; and
reconstructing a three-dimensional image based on the plurality of projection images of the subject when it is determined that the quality measure indicates suitable quality.

16. A method according to claim 15, wherein determining the quality measure associated with the plurality of projection images based on the local fluctuation measure comprises inputting the local fluctuation measure to a trained artificial neural network.

17. A system comprising:
an imaging system to acquire a plurality of projection images of a subject, each of the projection images acquired from a respective projection angle; and
a control system to:
determine, for each of the projection images, a center-of-light location in a first image region;
determine a local fluctuation measure based on the determined center-of-light locations;
determine a quality measure associated with the plurality of projection images based on the local fluctuation measure; and
acquire a second plurality of projection images of the subject before reconstructing a three-dimensional image based on the plurality of projection images when it is determined that the quality measure indicates unsuitable quality.

18. A system according to claim 17, wherein determination of the local fluctuation measure is based on differences in the center-of-light locations determined for projection images associated with adjacent projection angles.

19. A system according to claim 17, wherein the processor is to execute processor-executable process steps to cause the system to:

determine, for each of the projection images, a center-of-light location in a second image region, wherein determination of the local fluctuation measure comprises:

determination of a first local fluctuation measure based on differences in the center-of-light locations determined in the first image region for projection images associated with adjacent projection angles, determination of a second local fluctuation measure based on differences in the center-of-light locations determined in the second image region for projection images associated with adjacent projection angles, and determination of the local fluctuation measure based on the first local fluctuation measure and the second local fluctuation measure.

20. A system according to claim 19, wherein the processor is to execute processor-executable process steps to cause the system to:

determine a first center-of-light location for a first one of the projection images;

determine the first region and the second region of the first one of the projection images based on the determined first center-of-light location;

determine a second center-of-light location for a second one of the projection images; and determine the first region and the second region of the second one of the projection images based on the determined second center-of-light location.

* * * * *